Figure 8:
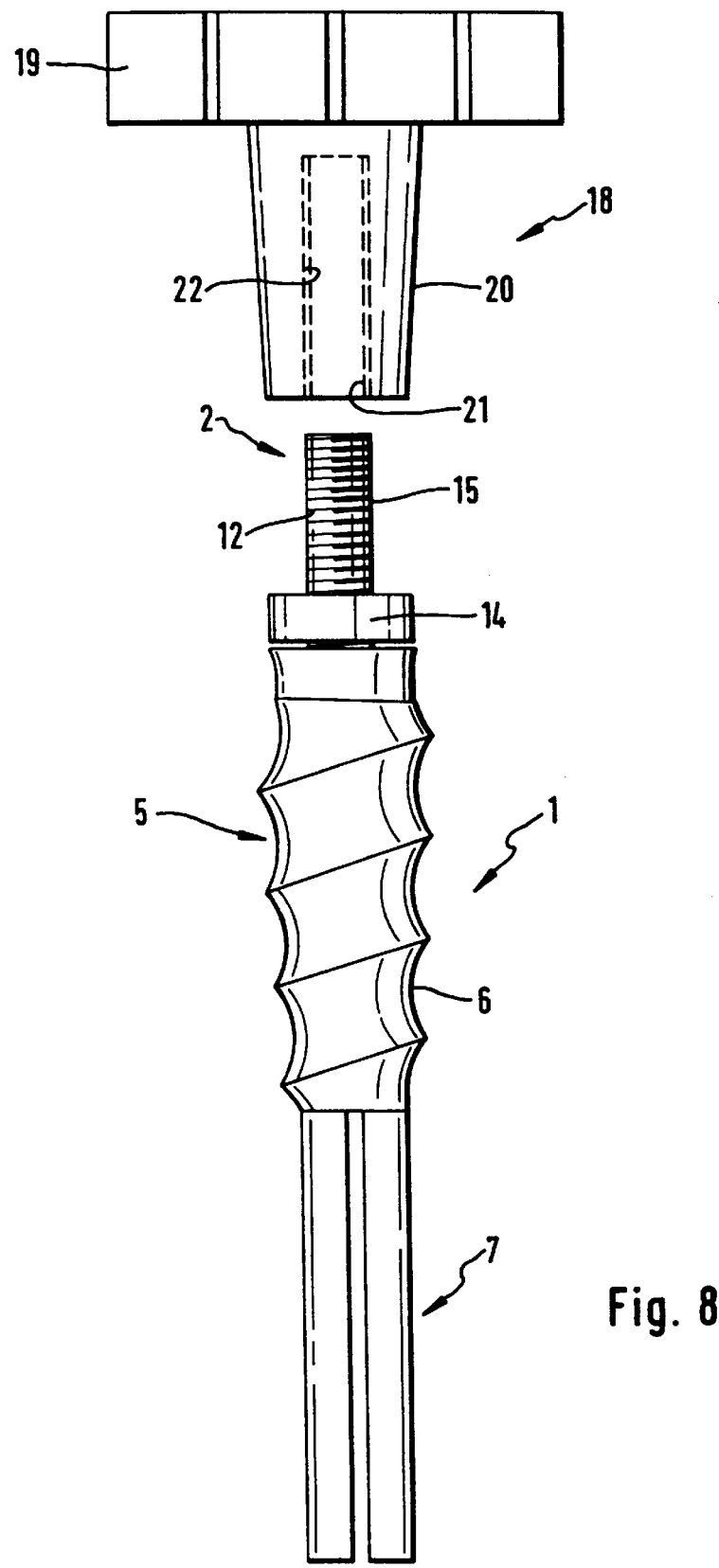

United States Patent
Bauer

[11] Patent Number: 6,007,337
[45] Date of Patent: Dec. 28, 1999

[54] JAW IMPLANT

[76] Inventor: Ernst Bauer, Eleonorenring 14, D-61231 Bad Nauheim, Germany

[21] Appl. No.: 08/765,854
[22] PCT Filed: May 7, 1996
[86] PCT No.: PCT/EP96/01901
§ 371 Date: May 2, 1997
§ 102(e) Date: May 2, 1997
[87] PCT Pub. No.: WO96/35393
PCT Pub. Date: Nov. 14, 1996

[30] Foreign Application Priority Data

May 12, 1995 [DE] Germany .............................. 19517459

[51] Int. Cl.$^6$ ...................................................... A61C 8/00
[52] U.S. Cl. ............................................. 433/173; 433/174
[58] Field of Search .................................... 433/173, 174, 433/175, 172, 176

[56] References Cited

U.S. PATENT DOCUMENTS

| | | | |
|---|---|---|---|
| 3,708,883 | 1/1973 | Flander . | |
| 4,406,623 | 9/1983 | Grafelmann et al. ................ | 433/174 |
| 4,588,381 | 5/1986 | Caracciolo ............. | 433/173 |
| 5,004,421 | 4/1991 | Lazarof ................. | 433/173 |
| 5,087,199 | 2/1992 | Lazarof ................. | 433/173 |
| 5,141,435 | 8/1992 | Lillard .................. | 433/176 |
| 5,211,833 | 5/1993 | Shirkhanzadeh ........ | 205/322 |
| 5,470,230 | 11/1995 | Daftary et al. ......... | 433/174 |
| 5,489,210 | 2/1996 | Hanosh ................. | 433/173 |

FOREIGN PATENT DOCUMENTS

| | | |
|---|---|---|
| 114955 | 8/1984 | European Pat. Off. . |
| WO 93/11717 | 6/1993 | WIPO . |
| WO 95/31152 | 11/1995 | WIPO . |

*Primary Examiner*—John J. Wilson
*Attorney, Agent, or Firm*—Marshall, O'Toole, Gerstein, Murray & Borun

[57] ABSTRACT

A set for producing a jaw implant has an implant body (1) that may be screwed into the jaw bones and an implant head (3) that may be secured to the implant body (1) to receive a prosthesis or prosthesis-supporting structure. The lower insertion section of the implant body (1) is designed as an expanding body (7) with several expanding elements (7) that may be spread after the implant body is screwed into the jaw bones. The base designed as an expanding body (7) gives the implant body (1) a good support on the osseous substance of the supporting cortical layer. Since the implant bodies (1) finds in the expanding elements (8) a multiple support on the cortical layer of the jaw bone, the forces axially transmitted to the implant body during mastication are better absorbed, improving the durability of the implant. The load is not concentrated on a single point but is rather distributed over a larger area. In a preferred embodiment, the implant body is an elongated hollow body whose insertion bottom section is slotted several times in the longitudinal direction to form the expanding elements (8). A pin (2) is screwed into the hollow body for spreading the expanding elements. The implant head (3) is designed as a screwable cap which can be screwed on the free end of the pin (2).

5 Claims, 3 Drawing Sheets

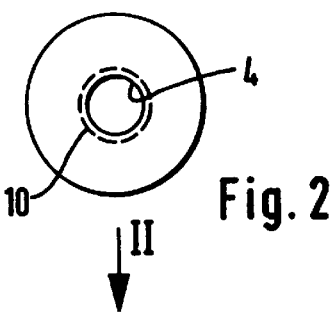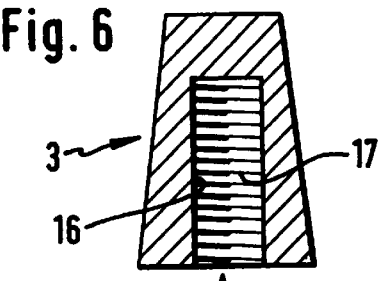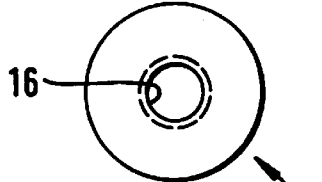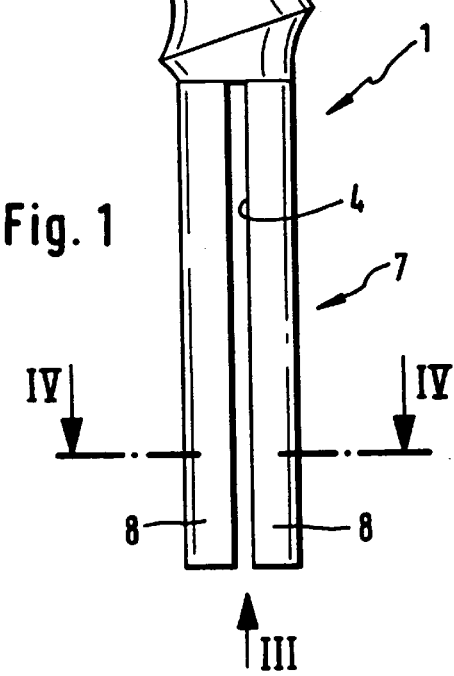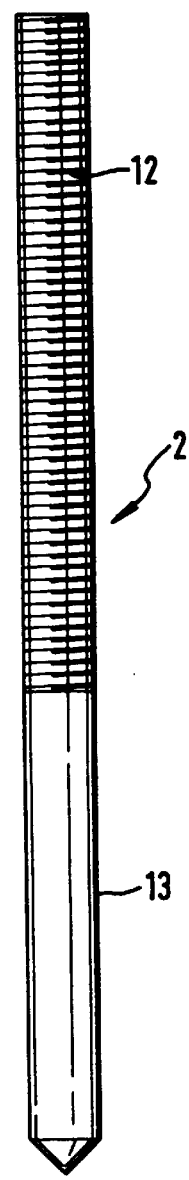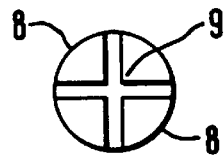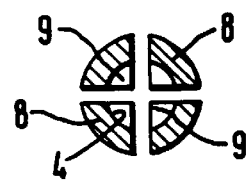

JAW IMPLANT

The invention concerns a jaw implant according to the principal clause of Patent claim 1.

Jaw implants are known in numerous versions. Known jaw implants include needle implants, blade implants and especially screw implants. Known screw implants have a conical implant body that can be screwed into the jawbone and is provided with an implant head to accept a false tooth or a subconstruction.

It has been shown that the design and use of screw bodies implanted subperiosteally or intraosteally is not without problems. Destruction of the bone substance by the relatively deep penetration of the cutting threads cannot be ruled out in the known screw implants. Primary stability, on which later retention is dependent and which is largely responsible for frictional bonding of the implant and bone, is not guaranteed owing to the destroyed tissue parts and the empty spaces occurring in the region of the implant. Special significance is assigned to the shape of the threads in screw implants. For example, DE-OS 31 36 602 proposed a screw implant having a conical screw shaft with a helical thread in order to impart greater strength to the implant in the implanted state.

EP-A-0 114 955 describes a jaw implant with a shaft implant body designed as an expansion body in its lower, insertion-side section. The known implant is not designed as a screw implant. It is introduced to a hole in the jaw bone and anchored by expansion of the implant foot.

For durable retention of the implant it is not only decisive that destruction of the bone substance be avoided during insertion of the threading, but also that the implant find support on both ends in the bone, i.e., the compact bone substance of the alveolar ridge and the counter-corticalis. The known screw implants must therefore be supported on the bone substance of the lower jaw bone opposite the entrance with the hemispherical tip of their conical screw shaft. However, it has been shown that, despite support, penetration of the known screw implants into the jaw bone because of high chewing pressure cannot be ruled out. The large axial forces, which exert severe loading on the bone tissue, can cause loosening of the implant so that loss of sealing can occur in the region of insertion of the implant body into the jaw bone, which represents a focus of infection.

The underlying task of the invention is to devise a screw implant of the type mentioned in the introduction that permits improved anchoring in the jaw bone and withstands high chewing pressures.

Solution of the task occurs according to the invention with the features stated in Patent claim 1.

The implant foot of the screw of the screwable implant body is designed in the set according to the invention for production of a jaw implant as an expansion body having several expansion elements that can be expanded laterally. The implant body finds adequate support on the bone substance of the counter-corticalis with the foot part designed as an expansion body. Since the implant body is multiply supported with the expansion elements on the counter-corticalis, the forces introduced axially to the implant body during chewing movements can be better supported so that the durability of the implant is improved. The load is not concentrated at a single point, but is distributed over a larger region.

Although the region in which the implant body is supported on the counter-corticalis is enlarged relative to the known screw implants, the implant body of the set according to the invention requires only relatively limited intervention in which only little bone substance is removed. Expansion of the foot part by expansion of the expansion elements occurs only when the implant has been screwed into the jaw bone.

The expansion elements create not only a widened support surface, but are pressed into the contacted spongy bone substance, i.e., the bone tissue, so that a frictional bond and high stability are achieved. Another advantage is that the intermediate spaces lying between the expansion elements are penetrated by the spongy bone substance and the implant body can thus intergrow firmly with the bone. Durable fixation of the implant body in the jaw bone is thus achieved.

Advantageously, the implant body is an elongated hollow element having a continuous channel in which the foot part of the hollow element is multiply slit in the longitudinal direction to form the expansion elements and the continuous channel tapers in the region of the foot part. The tongue-like expansion elements can therefore be simply expanded by screwing a pin into the sleeve-like implant body. This design of the implant body is advantageous in that the pin for expansion of the expansion elements can simultaneously serve to anchor the implant head or the subconstruction.

The sleeve-like implant body can be designed in one piece. For manufacturing reasons, however, it can be advantageous to produce the implant body from two parts, one part of which includes the screw threads for insertion of the implant body and the other part includes the expansion body.

To achieve adequate support, in a preferred variant, the implant body is slit cross-wise to form four expansion elements. In order to permit expansion of the expansion elements, these preferably have inward protruding projections. However, expansion of the expansion elements can also be achieved by widening the pin on its insertion end, whereas the channel in the region of the bottom of the implant body has a cross section that remains constant over its length.

The implant head is advantageously designed as a screw cap. In order to be able to screw the implant head onto the pin, the length of the pin is dimensioned so that the pin protrudes above the top of the implant body even when it has been fully screwed into the implant body. The false tooth can be fastened to the preferably conical screw cap. The screw cap, however, can also be used to receive the known subconstructions for the false tooth.

In order to obtain tight sealing, the top of the implant body is preferably designed as a conical screw. A hole is first drilled with an implant drill for insertion of the implant. The implant body is then guided axially through the predrilled implant bed.

The parts forming the implant, namely the implant body, the pin and the implant head, preferably consist of a titanium alloy and the surface of the parts is passivated with a protective layer of titanium oxide in order to guarantee good compatibility.

A practical example of the invention is further explained below with reference to the drawings.

Figure 9:
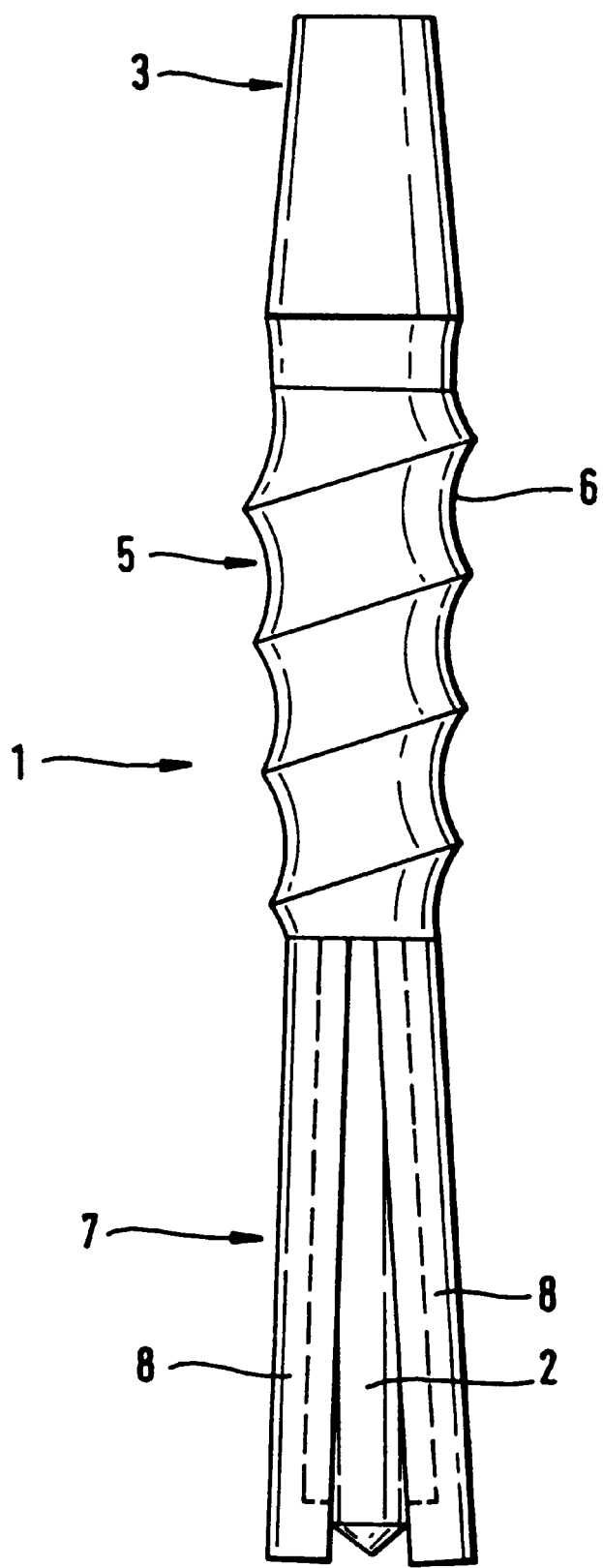

In the drawings:

FIG. 1 shows in a side view the implant body of the set for production of a jaw implant, FIG. 2 shows a view of the implant body in the direction of arrow II of FIG. 1, FIG. 3 shows a view of the implant body in the direction of arrow III—III of FIG. 1, FIG. 4 shows a section through the implant body along line IV—IV of FIG. 1, FIG. 5 shows in a side view the pin belonging to the set for production of the jaw implant, FIG. 6 shows a longitudinal section through the implant head belonging to the set for production of the jaw implant, FIG. 7 shows the implant head viewed in the direction of arrow VII of FIG. 6, FIG. 8 shows an exploded view in a side view of the implant body with pin, mounting sleeve and a turning aid for screwing of the implant body, and FIG. 9 shows in a side view the implant body with the expanded expansion elements and the screwed-on implant head.

The set for production of a jaw implant has an implant body 1 that can be screwed into the jaw bone (FIG. 1), a pin 2 that can be screwed into the implant body 1 (FIG. 5) and an implant head 3 that can be screwed onto the pin 2 (FIG. 6) to accept the false tooth or a subconstruction not shown in the figures. The implant body 1 is further explained below with reference to FIGS. 1 to 4.

FIG. 1 shows the implant body 1 in a side view. The implant body 1 is an elongated hollow element provided with a continuous channel 4. The upper half of the implant body 1 is designed as a conical screw 5 with concave threading 6, in which the conical screw narrows toward the insertion-side, lower end of implant body 1. On the upper half of the implant body 1, a cylindrical expansion body 7 is connected. For this purpose the lower half of the implant body 1 is slit crosswise in the longitudinal direction to form four elongated tongue-shaped expansion elements 8 (FIG. 3). The expansion elements 8 each have an inward pointing projection 9 on their lower end (FIG. 4).

The channel 4 of the implant body 1 has a circular cross section (FIG. 2). The partial section of hole 4 extending through the upper half of the implant body 1 is provided with internal threading 10, whereas the partial section of hole 4 extending through the lower half of implant body 1 is unthreaded.

FIG. 5 shows the pin 2 belonging to the set for production of the jaw implant in a side view. The pin 2, which can be screwed into hole 4 of implant body 1, has external threading 12 corresponding to the threaded hole of the implant body, which extends to the center of pin 11. The lower unthreaded section 13 of the pin has a length corresponding to the length of the lower longitudinally slit half of implant body 1. Pin 2 itself is longer than implant body 1.

FIG. 6 shows the implant head 3 belonging to the set for production of the jaw implant, which can be screwed onto part 15 of threaded pin 2 extending above implant body 1. The conical implant head 3 designed as a screw cap has an axial hole 16 with an internal threading 17 corresponding to the external threading 12 of pin 2 (FIGS. 6 and 7).

Implant body 1, pin 2 and implant head 3 consist of a titanium alloy and the surface of the parts is passivated with a protective layer of titanium oxide according to ASTM F 86-68.

The working steps required for insertion of the implant are explained below with reference to FIGS. 8 and 9.

For insertion of the implant, pin 2 is first screwed loosely by hand into implant body 1 until the front tip lies against the protruding projections 9 of expansion element 8. A spacer sleeve 14 is then placed on pin 2. The set also includes a turning aid 18 to screw implant body 1 into the jaw bone. The turning aid 18 consists of a knurled rotary head 19 with a shaft 20 having an axial hole 21 provided with internal threading 22 corresponding to the external threading 12 of pin 2. Turning aid 18 and implant body 1 are screwed together with interpositioning of spacer sleeve 14 without pin 2 being further turned into the implant body so that the expansion elements 8 would be expanded.

After preparation of implant body 1, a narrow channel is drilled into the jaw bone with an implant drill whose diameter corresponds to the diameter of the lower cylindrical section of implant body 1. The precise depth of the alveolar ridge up to the counter-corticalis can now be measured by means of the probe through the drilling channel and the length of the implant body checked. Thereupon implant body 1 is screwed into the jaw bone by means of turning aid 18. Turning aid 18 is then unscrewed in simple and continuous consecutive working steps, spacer sleeve 14 is removed and the turning aid screwed back on. Pin 2 can now be fully screwed into the implant body 1 so that the expansion elements 8 expand laterally. The angle by which the expansion elements 8 are expanded relative to the longitudinal axis of the implant body should be between about 5 and 20 degrees. After unscrewing off turning aid 18, a plastic protective sleeve provided with internal threading (not shown in the figures) is screwed onto the protruding section 15 of pin 2 in order to avoid intergrowth of the gums with the pin. The protective cap is later removed again and the conical implant head 3 is screwed onto pin 2 instead of the protective cap (FIG. 9). The false tooth or subconstruction for the false tooth can then be attached to the implant head in the known manner.

I claim:

1. Set for production of a jaw implant, comprising:
  a) an implant body screwable into a jawbone, the implant body comprising an elongated hollow element defining a continuous, longitudinal channel, said implant body having an insertion-site lower section that is multiply slit in the longitudinal direction to form expansion elements, said implant body having an upper section comprising a conical screw provided with external concave threading, wherein said conical screw narrows toward said lower section;
  b) a pin provided with external threading that can be screwed into the continuous channel of the implant body for expansion of the expansion elements, the length of the pin being such that a portion of the pin protrudes above the implant body when the pin is screwed into the implant body; and
  c) an implant head comprising a screw cap such that the implant head can be attached to the portion of the pin protruding above the implant body to receive a false tooth or a subconstruction.

2. Set for production of a jaw implant according to claim 1 wherein the expansion elements have inward pointing projections.

3. Set for production of a jaw implant according to claim 1 wherein the implant body is slit crosswise to form four expansion elements.

4. Set for production of a jaw implant according to claim 1 wherein the implant body, the implant head, and the pin are formed of a titanium alloy and the surface of each of the implant body, the implant head, and the pin is passivated with a protective layer of titanium oxide.

5. Set for production of a jaw implant according to claim 1, wherein said longitudinal channel tapers in the region of the lower section of the implant body.

* * * * *